(12) United States Patent
Rix

(10) Patent No.: US 6,709,443 B1
(45) Date of Patent: Mar. 23, 2004

(54) NOSEBLEED LIP PACK

(76) Inventor: Amy D. Rix, 6507 Glen Forest Dr., Chapel Hill, NC (US) 27514

( * ) Notice: Subject to any disclaimer, the term of this patent is extended or adjusted under 35 U.S.C. 154(b) by 0 days.

(21) Appl. No.: 10/232,114

(22) Filed: Aug. 30, 2002

(51) Int. Cl.$^7$ ............................................. A61M 29/00

(52) U.S. Cl. ..................................................... 606/196

(58) Field of Search ................................ 606/196, 191, 606/197, 199, 204.45; 604/286

(56) References Cited

U.S. PATENT DOCUMENTS

| | | | |
|---|---|---|---|
| 3,850,176 A | * 11/1974 | Gottschalk | ................... 606/196 |
| 3,884,241 A | 5/1975 | Walker | |
| 3,903,893 A | 9/1975 | Scheer | |
| 3,935,859 A | 2/1976 | Doyle | |
| 4,457,756 A | 7/1984 | Kern et al. | |
| 4,646,739 A | 3/1987 | Doyle | |
| 4,820,266 A | 4/1989 | Berry | |
| 4,883,465 A | 11/1989 | Brennan | |
| 5,011,474 A | 4/1991 | Brennan | |
| 5,094,233 A | 3/1992 | Brennan | |
| 5,330,445 A | 7/1994 | Haaga | |
| 5,336,163 A | 8/1994 | DeMane et al. | |
| 5,383,891 A | 1/1995 | Walker | |
| 5,391,179 A | 2/1995 | Mezzoli | |
| 5,447,502 A | 9/1995 | Haaga | |
| 5,527,351 A | 6/1996 | Friedman | |
| 5,584,822 A | 12/1996 | Lively et al. | |
| 5,584,827 A | 12/1996 | Korteweg et al. | |
| 5,599,284 A | 2/1997 | Shea | |
| 5,601,594 A | 2/1997 | Best | |
| 5,700,252 A | * 12/1997 | Klingenstein | ............... 606/196 |
| 5,713,839 A | 2/1998 | Shea | |
| 5,899,918 A | 5/1999 | Knott et al. | |

OTHER PUBLICATIONS

Culbertson, "Epistaxis", *The Nose, Paranasal Sinuses, Face, and Orbit*, Chapter 27, p. 719–720.
Web Page for Dr. Joseph F. Smith Medical Library, "Nosebleed", http://www.chclibrary.org, printed Apr. 25, 2002.
Culbertson et al., "Epistaxis" *The Nose, Paranasal Sinuses, Face, and Orbit*, Chapter 32, p. 672–674.
Saundes, "Epsitaxis", Chapter 5.
Yoo et al., "Epistaxis", *Department of Otolaryngology, UTMB, Grand Rounds*, Jan. 5, 1994, http://www.utmb.edu, printed Jun. 2, 2002.
Web Page for Health Square, "Ear, Nose and Throat Disorders", http://www.healthsquare.com, printed Apr. 22, 2002.
Web Page for Nose and Paranasal Sinuses, http://www.bcm.tmc.edu, printed Jun. 5, 2002.
Chang, "Nose Anatomy", http://www.emedicine.com, printed Jun. 2, 2002.
Web Page for "Henry Gray, Anatomy of the Human Body" http://www.bartleby.com, printed Apr. 24, 2002.
"607 Arteries to Walls of Nasal Cavity".
Web Page for "Anatomy as Related to Rhinoplasty", http://www3.utsouthwestern.edu, printed Apr. 24, 2002.
*Diseases of the Nasal Septum*, p. 41.
Web Page for Hughston Health Alert, "Nosebleeds (Epistaxis)", http://www.hughston.com, printed May 28, 2002.

(List continued on next page.)

*Primary Examiner*—Kevin T. Truong
(74) *Attorney, Agent, or Firm*—Moore and Van Allen, PLLC; Jennifer L. Skord

(57) ABSTRACT

A device for treatment of nosebleeds having an elongated body configured to be positioned between the upper gum and the portion of the face below the nose and above the top lip of a human. When so positioned intra-orally, the device exerts pressure on an area of nasal vascularization of the human. Also, a nosebleed package having a sterile inside environment and a nosebleed device packaged therein, and a box containing a plurality of nosebleed packages.

9 Claims, 5 Drawing Sheets

OTHER PUBLICATIONS

*The Nose and Paranasal Sinuses*, Chapter 4, p. 279.

*Textbook of Otolaryngology*, p. 224.

Berkowitz, "Nosebleeds in Pediatrics", *Primary Care Approach*.

Cordes et al., "Epistaxis", *Dept. of Otolaryngology, UTMB, Grand Rounds*, Oct. 16, 1996, http://www.utmb.edu, printed May 20, 2002.

Web Page for ENTNet, "Nosebleeds", http://www.entnet.org, printed Apr. 22, 2002.

Web Page for Virtual Hospital, "Otolarynology: Nose", http://www.vh.org, printed Jun. 3, 2002.

Averill, "Epistaxis", Sep. 22, 2000, http://web2.chm.msu.edu, printed Jun. 4, 2002.

Shippert, "Epistaxis and Nasal Packs", Jun. 15, 1999, http://www.shippertmedical.com, printed May 28, 2002.

Web Page for Healthseva, Nosebleeds, http://www.healthseva.com, printed May 17, 2002.

* cited by examiner

NOSEBLEED LIP PACK

FIELD OF THE INVENTION

The present invention relates, in general, to the treatment of epistaxis, more commonly referred to as nosebleed. More particularly, the present invention relates to a device and a method for the treatment of nosebleed, as well as a nosebleed package containing the device.

BACKGROUND

Nosebleeds are a common non-physiological cause of bleeding. The majority of nosebleeds in humans occur as a result of hypertension, long-term infection, leukemia, vitamin K deficiency, blows to the nose, sneezing, nasal drug abuse, allergic rhinitis, use of blood thinners or children picking their noses with sharp fingernails. Nosebleeds often occur without warning and can be extremely dangerous if not controlled promptly and properly. Excessive loss of blood may result in unconsciousness and death. Children and the elderly are particularly susceptible to serious, acute nosebleeds.

To the best of applicant's knowledge, the most pertinent of all the prior art methods for control of nosebleeds is disclosed in "Nosebleeds in Pediatrics", which is a chapter written by Carol Berkowitz in a book entitled *Primary Care Approach* (published 2000) by Stanley H. Inkelis, M.D. This reference discloses that children who are actively bleeding through the nose should be positioned sitting upright while leaning forward slightly and that direct pressure should be applied and that a cotton dental roll may be placed under the upper lip to compress the labial artery in older children for whom concern about displacement and possible aspiration of the cotton is minimal.

General background information relevant to attempts to control nosebleeds can be found in U.S. Pat. Nos. 5,899,918; 3,884,241; 4,457,756; 4,646,739; 5,383,891; 5,584,822; 5,584,827; 5,391,179; and 5,011,474. These patents describe devices and methods for controlling nosebleeds that involve pinching the nose with external or internal clips, packing the nasal cavity with absorbent tampons, or using special hemostatic devices that require skilled medical training. However, these devices and methods suffer from numerous disadvantages.

More specifically, the described methods of pinching the nose seek to control nosebleeds by applying pressure to an area of the septum known as Kiesselbach's plexus (also called Little's area). However, pinching the nose is not only uncomfortable but also is difficult for small children to administer to themselves.

Likewise, the described tampons for packing the nasal cavity seek to control nosebleeds by applying pressure to Kiesselbach's plexus, and such tampons are both uncomfortable and difficult to administer. Moreover, the tampons can damage the nasal passageway due to necrosis from undue pressure or overpacking. Also, prolapse of the tampon into the pharynx is a dangerous risk. Hence, use of nasal tampons in small children and the elderly must be continually monitored. Additionally, the tampon may dry out and stick to the delicate nasal mucosa, making removal of the packing painful and presenting a risk of the bleeding recurring.

Furthermore, both pinching the nose with the fingers or other device and packing the nose with a tampon interfere with normal nasal breathing. Consequently, the patient must breath through the mouth, which may result in uncomfortable drying of the mouth, throat irritation, and middle-ear complications.

With regard to the number of sophisticated hemostatic devices to control nosebleeds on the market, such sophisticated devices are not only time-consuming to administer but also require the skills of a physician or other trained medical personnel in a medical treatment facility, such as a hospital. Thus, these devices are unsuitable for the prompt treatment of the vast majority of nosebleeds that happen in the home, office, or school. Nevertheless, home remedies, such as tilting the head, applying cold compresses to the nose or manually compressing the nose, typically are ineffective in stopping nosebleeds promptly.

Hence, a long felt need still exists for a readily available device and method for treating nosebleeds that can be effectively used by untrained laypersons away from medical treatment facilities.

SUMMARY OF THE INVENTION

Accordingly, the present invention provides a device for treatment of nosebleeds. The device comprises an elongated body configured to be positioned between the upper gum and the portion of the face below the nose and above the top lip of a human so as to exert pressure on an area of nasal vascularization of the human.

Also, the present invention provides a method of treating a nosebleed in a human having a nosebleed. The method comprises providing a nosebleed device comprising an elongated body configured to be positioned between the upper gum and the portion of the face below the nose and above the top lip of the human, and positioning the device between the upper gum and the portion of the face below the nose and above the top lip of the human so as to exert pressure on an area of nasal vascularization of the human, and achieving alleviation of the nosebleed.

Additionally, the present invention provides a nosebleed package comprising in combination a container having a sterile inside environment and a device for treating nosebleeds, the device being disposed inside the container and comprising an elongated body configured to be positioned between the upper gum and the portion of the face below the nose and above the top lip of a human so as to exert pressure on an area of nasal vascularization of the human.

Furthermore, the present invention provides a box containing a multiplicity of nosebleed packages comprising individually packaged nosebleed devices. Each nosebleed package comprises a nosebleed device in combination with a container having a sterile inside environment, and each nosebleed device is disposed inside the container. Also, each nosebleed device comprises an elongated body configured to be positioned between the upper gum and the portion of the face below the nose and above the top lip of a human so as to exert pressure on an area of nasal vascularization of the human.

Therefore, it is an object of the present invention to provide a device and a method for treating nosebleeds that require neither medical treatment facilities nor detailed medical training or expertise for use of the device and method.

It is another object of the present invention to provide a nosebleed treatment device in sizes appropriate for different age groups or mouth sizes.

It is still another object of the present invention to provide a device for the treatment of nosebleeds such that the device may be disposed of after a single use.

It is a further object of the present invention to provide a device for treating nosebleeds where the device is supplied in a container having a sterile inside, the container being suitable for convenient transport and single-use application of the device.

It is an advantage of the present invention that the device causes minimal, if any, discomfort, does not interfere with normal nasal breathing, and can be effectively and quickly used by laypersons without medical training.

Other features, aspects and advantages of the present invention will become better understood with reference to the following description, accompanying drawings and appended claims.

DESCRIPTION

Figure 1:
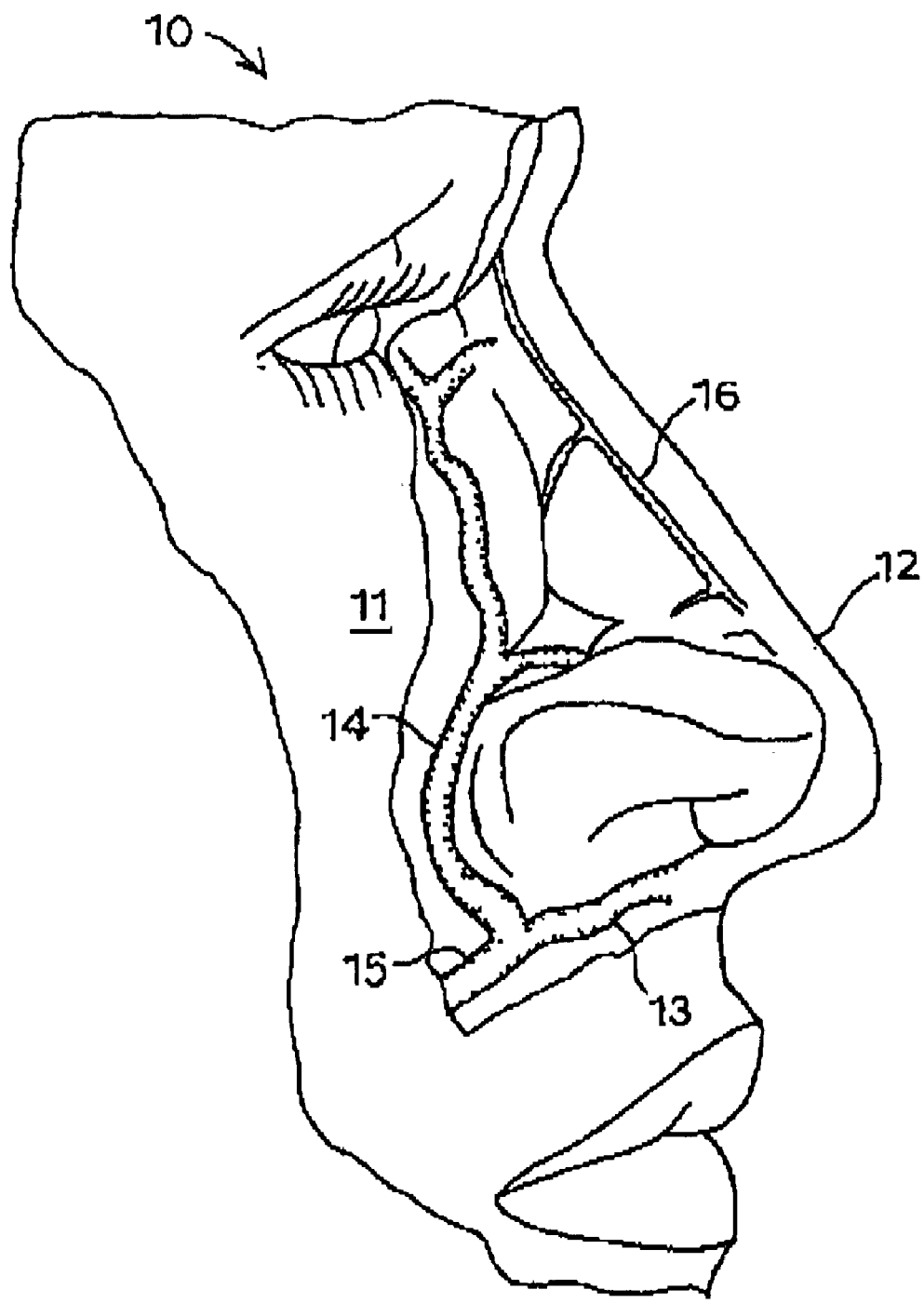
FIG. 1 shows a side elevation view of the nasal area of a human face, with a portion of the outer layer of tissue cut-away in the nasal area to show schematically the anatomical configuration of the major arteries supplying blood to the nose.

Although the nosebleed devices are described below in a preferred embodiment with a circular cross section, the devices could also have a non-circular cross-sectional shape that could increase the surface area. Other cross-sectional shapes may include, but are not limited to, oval, triangular, square, rhomboid, parallelepiped, pentagon, hexagon, and the like.

Hence, the term "diameter" as used here is intended to mean the transverse length of the cross section, regardless of whether the cross section is circular or some other shape.

Suitable diameters for the inventive devices described below may range from about 4 mm to about 12 mm, and of course, the diameter may be from about 5 mm to about 11 mm, or from about 6 mm to about 10 mm.

Typical lengths of the device range from about 30 mm to about 80 mm, more particularly from about 35 mm to about 75 mm, more particularly from about 40 mm to about 70 mm, and even more particularly about 50 to about 60 mm.

The diameter and/or the length of the device can vary depending on several factors such as the size of the person to be treated and the like. In general, a device with a smaller diameter and/or a shorter length will be suitable for a small person, for instance, a child.

The phrase "area of nasal vascularization" as used here is to be broadly construed. The area of nasal vascularization includes, but is not limited to, the superior labial artery and other arteries in the face and head that are conduits to Kisselbach's plexus, such as the angular artery, the facial artery, the anterior ethmoidal arteries, the posterior ethmoidal arteries, the sphenopalatine artery, or combinations thereof.

The term "compression padding" as used here refers to a part of the nosebleed device that should enhance the effect of the device on the area nasal vascularization. The compression padding is disposed on a portion of the device, in one embodiment as further described below.

The terms "treatment" and "treating" as used here in regard to a method of treating a nosebleed in a human having a nosebleed refer, in general, to accelerating the cessation of a nosebleed and/or accelerating the slowing of the nosebleed. Treatment with the inventive device should result in alleviation of a nosebleed by stopping and/or slowing the flow of blood into Kiesselbach's plexus so that natural coagulation mechanisms are enabled.

Nevertheless, the inventive nosebleed device is primarily intended for treatment of an anterior nosebleed. An anterior nosebleed is one that comes from the front part of the nose and begins with a flow of blood out of one or both nostrils if the patient is sitting up or standing, whereas a posterior nosebleed is one that comes from deep in the nose and flows down the back of the mouth and throat even if the patient is sitting up or standing. The anteroinferior portion of the nasal septum, generally about 5 cm from the tip of an adult nose, known as Kiesselbach's plexus or Little's area, is the most common part of the nose involved in anterior nosebleeds. Kiesselbach's plexus is supplied blood by the anterior and posterior ethmoidal arteries, the sphenopalatine artery, and the septal branches of the superior labial artery. On the other hand, the turbinate or nasal wall is the most common part of the nose involved in posterior nosebleeds, and significant bleeding, i.e., a nasal hemorrhage, may occur during a posterior nosebleed from a branch of the sphenopalatine artery.

It is not believed that the nosebleed device provided here functions adequately with respect to efficient hemostatis, such as after septal, sinus, or rhinoplastic surgery. Further, the device is not believed to function adequately with respect to abating nasal hemorrhage (posterior nosebleed), the posterior nosebleed requiring a trained medical person to control significant bleeding, usually from ruptured major arteries and blood vessels over substantially all parts of the nasal cavity.

Hence, by the phrase "alleviate the nosebleed" as used here, it is not intended to include stopping the nosebleed in every instance as some of those instances will be a nasal hemorrhage from a posterior nosebleed, in which instances the nosebleed most likely will not stop and so professional medical assistance should be sought to stop the bleeding.

The present invention is directed to satisfying the need for a device and method of treating nosebleeds that can be effectively used not only by medical professionals but also in the home or other non-medical facilities by non-medical personnel. The invention comprises a nosebleed device that preferably is a generally cylindrical shaped pad that is used as a lip pack. The lip pack is placed between the upper gum and the portion of the face between the top lip and the bottom of the nose.

The lip pack is configured so as to fit comfortably along the anatomical contours of the portion of the mouth where the lip pack is placed. The lip pack is further configured so as to apply hemostatic pressure on an area of nasal vascularization, typically the superior labial artery. To the best of applicant's knowledge, there are no known devices presently commercially available that are designed to treat nosebleeds by the application of pressure on the area of nasal vascularization, such as the superior labial artery, from inside the mouth.

The pad for use as a lip pack may be constructed of materials such as gauze, cotton, polyurethane, rayon, rubber, polysorbate, polyvinyl alcohol, and the like. Preferably, a material should be relatively soft and pliable. Even more preferably, dense porous materials are preferred as they absorb liquids such as saliva or water, and thus, may be wetted, for instance with water, prior to positioning, which should make insertion and retention of the inventive nosebleed device more comfortable. For instance, a suitable dense porous material is foamed polyvinyl alcohol.

The portion of face below the nose and above the top p and also the natural tightness of the interface of that portion with the upper gum should hold the nosebleed device in place. The effect of the nosebleed device may be augmented by applying gentle pressure with a finger or fingers above the top lip, directly over the region occupied by the pad. Used as directed, the nosebleed device should be painless, and should not interfere with breathing or eating. Moreover, the device avoids the complications from undue pressure or overpacking of the nasal cavity attendant many prior art devices. The ease of use of the device makes it suitable for self-application and self-removal by the average layperson, including children and the elderly.

The lip pack treats nosebleeds by exerting pressure on an area of nasal vascularization, for instance the major arteries supplying blood to the nose. Treatment of a nosebleed with the inventive lip pack should result in control of the flow of blood to the nose such that the flow of blood is curbed or slowed. Suitably, treatment of the nosebleed is to the extent of stopping the flow of blood. If the nosebleed does not abate within approximately 30 minutes, the patient should seek medical attention from a trained professional, as most likely the nosebleed is the posterior kind.

In order to treat a nosebleed quickly and effectively without the aid of medical personnel, a preferred embodiment of the device comprises a lip pack composed of a soft, flexible pad that can be easily positioned between the upper gum and the portion of the face beneath the nose and above the top lip, the pad being a flattened cylinder, i.e., generally elliptical in cross-section, to apply hemostatic pressure to the major arteries supplying blood to the nose.

In an even more preferable embodiment, a portion of the lip pack has longitudinally disposed compression padding. When the lip pack is positioned intra-orally, the compression padding should be in the direction that is upward toward the nose so as to increase the pressure on the area of nasal vascularization as compared to a lip pack absent the extra compression padding.

Additionally, the lip pack preferably is packaged in a container having a sterile inside, but still typically is inexpensive, simple to use, and can easily be carried in a purse or pocket, much like BAND-AID® brand bandages marketed by Johnson & Johnson. When the lip pack is needed, a nosebleed victim can remove the lip pack from its sterile packaging and self-apply the lip pack to control a nosebleed without the assistance of a medical professional.

With reference now to the drawings, where like reference numerals designate corresponding or similar elements through the several views, shown in FIG. 1 is a side elevation view of a human face 10, with a portion of the outer layer of tissue cut-away to show the major areas of nasal vascularization 11 of the nose 12, including, but not limited to, the superior labial artery 13, the angular artery 14, and the facial artery 15. The superior labial artery 13 is the primary source of blood to the nose 12, eventually branching into a plexus of small vessels known as Kisselbach's plexus 16 (also known as Little's area).

Figure 2:
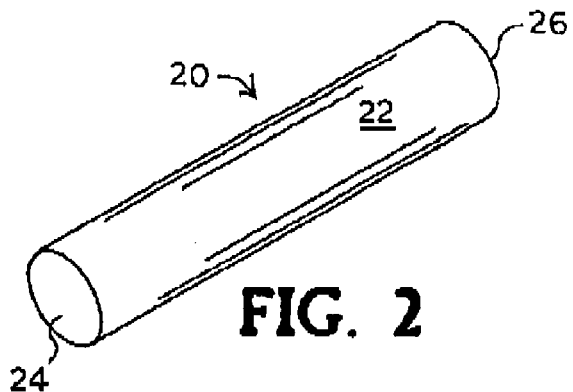
FIG. 2 shows a perspective view of one embodiment of the inventive nosebleed device.

FIG. 2 shows a three-dimensional view of an inventive device for treating nosebleeds depicted in one embodiment as a lip pack 20. In this embodiment of the invention, the nosebleed device/lip pack 20 includes an elongated body 22 that is generally circular in cross section and that terminates in first and second ends 24, 26. At least one of the ends 24, 26 of the lip pack 20 may be tapered, such as to approximately a 45° angle (not shown, see FIG. 4). The design of the lip pack 20 is suitable for self-application.

Thus, the lip pack 20 is generally configured in the shape of a cylinder so as to fit comfortably between the upper gum (not shown) and the portion of the face beneath the nose and above the top lip (not shown). The large adult-sized lip pack 20 may be about 60 to about 70 mm in length and the next smaller adult-sized lip pack 20 may be about 50 to about 60 mm in length, whereas the child-sized lip pack 20 may be about 30 to about 40 mm in length.

The lip pack 20 is preferably made of a pliable material so that the lip pack 20 can conform, such as by curving or flattening, to the anatomical contours of the mouth (not shown) after intra-oral placement. Also preferably, the lip pack 20 is made of a material that absorbs liquids, such as saliva and/or water.

As discussed above, the lip pack may be composed of a soft, resilient material such as gauze, cotton, rubber, rayon, polyurethane, polysorbate, polyvinyl alcohol, or combinations thereof, and preferably is a dense porous material. The advantage of such a resilient material is that it readily conforms to the anatomical contours of the mouth, and thus, is comfortable to use. For situations where reuse of the lip pack is desirable, the lip pack may be made of plastic or rubber. Techniques for manufacturing pads of this kind of material in a generally cylindrical shape are well known to those skilled in the art.

Figure 3:
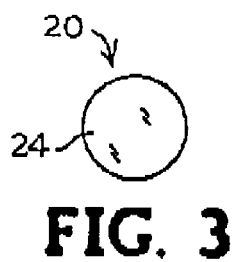
FIG. 3 shows a vertical cross-sectional view taken along the line 3—3 of FIG. 2.

FIG. 3 shows a cross-sectional view of the nosebleed device/lip pack 20 taken along line 3—3 of FIG. 2, in order to illustrate better the generally circular cross section. The large adult-sized lip pack 20 may have a diameter of about 10 to about 12 mm and the next smaller adult-sized lip pack 20 may have a diameter of about 8 to about 10 mm, whereas a child-sized lip pack 20 may have a diameter of about 4 to about 6 mm.

Figure 4:
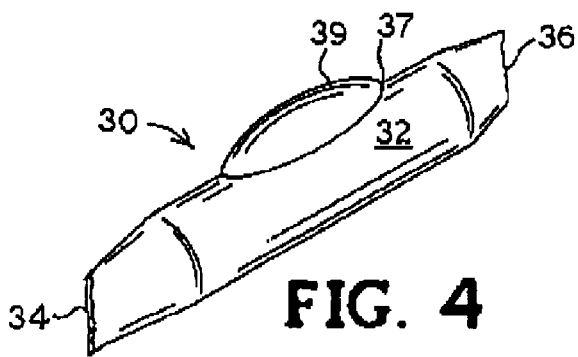
FIG. 4 shows a perspective view of another embodiment of the inventive nosebleed device having a portion with compression padding.

FIG. 4 shows a perspective view of another embodiment of the inventive device for treating nosebleeds illustrated as a lip pack 30. Lip pack 30 is of generally circular cross section, but shown as being somewhat more oval or elliptical as compared to lip pack 20 depicted in FIGS. 2 and 3. The nosebleed device/lip pack 30 includes an elongated body 32, and first and second ends 34, 36, shown in a preferred embodiment as tapered. Of course, only one of the two ends 34, 36 may be tapered. Also preferably, a portion 37 of the lip pack 30 further includes an element of compression padding 39 disposed longitudinally on the portion 37 of the lip pack 30.

The lip pack 30 may be of unitary construction so that the compression padding 39 is integral with the lip pack 30, or the lip pack 30 may be constructed so that a separate compression padding 39 is attached to the lip pack 30. Thus, the compression padding 39 may be composed of the same material as the rest of the lip pack 30, or a different material, all of these materials preferably being chosen from one or more of those noted above. The purpose of having the compression padding 39 is to exert more pressure on the area of nasal vascularization after intra-oral placement of the lip pack 30.

The compression padding 39 in the child and adult versions of the lip pack 30 would be appropriately proportioned so as to apply hemostatic pressure over a small or larger area, respectively. In general, the compression padding 39 should be about 1 to about 4 mm, more preferably about 2 to about 3 mm thick and should have a length about a quarter to about two-thirds, more preferably about a third to about a half of the length of the lip pack 30.

Figure 5:
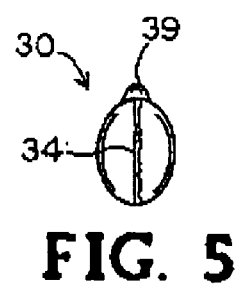
FIG. 5 shows a vertical cross-sectional view taken along the line 5—5 of FIG. 4.

FIG. 5 shows a cross-sectional view taken along line 5—5 of the nosebleed device/lip pack 30 in FIG. 4 in order to illustrate better the longitudinal disposition of the compression padding 39 on a portion 37 of the lip pack 30. As illustrated, the compression padding 39 is disposed toward an end of the longest transverse of the generally oval cross section.

Figure 6:
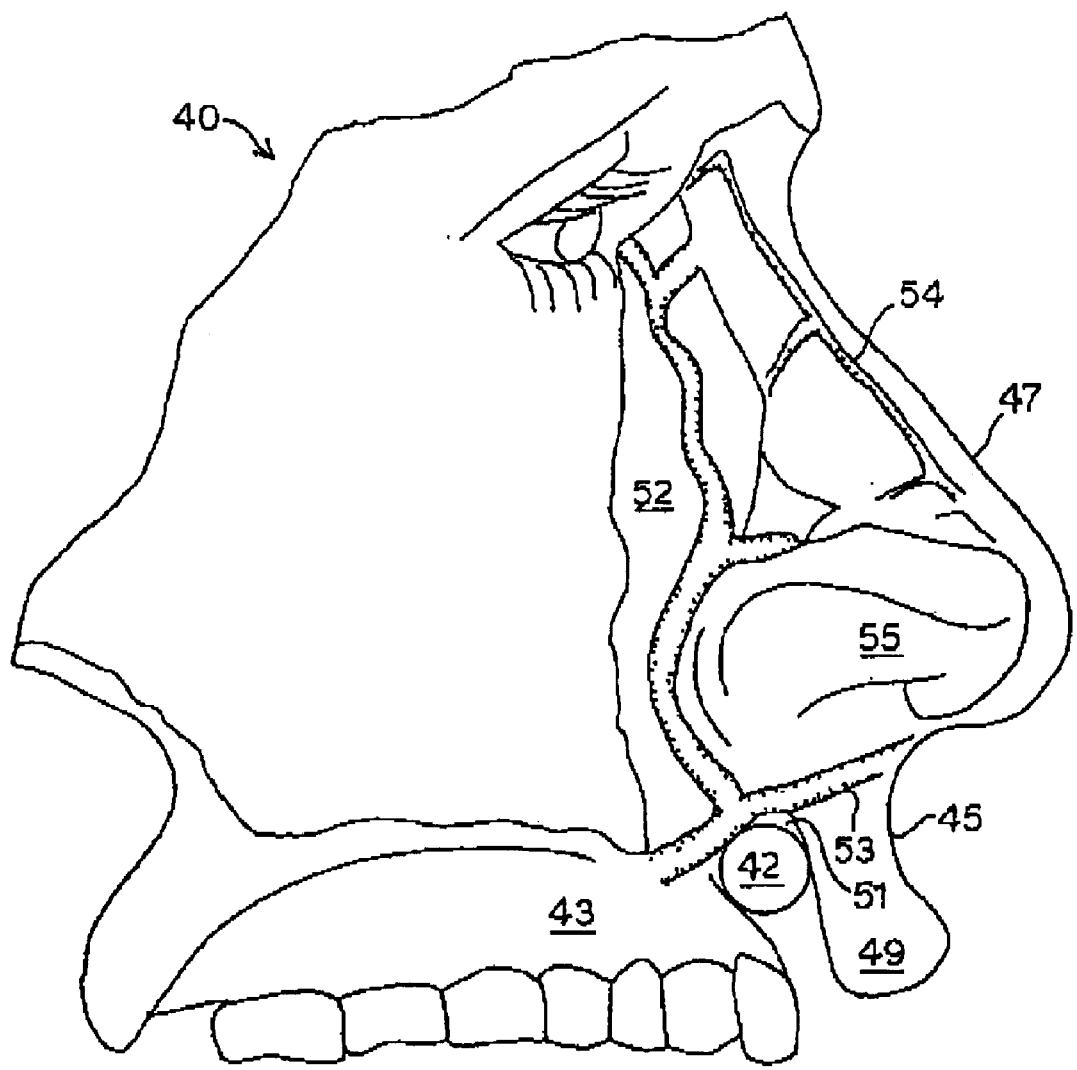
FIG. 6 shows a side elevation view of the nasal area of a human face, with a portion of the outer layer of tissue cut-away in the nasal area to show schematically the anatomical configuration of the major arteries supplying blood to the nose in relation to the placement of an embodiment of the inventive nosebleed device to help illustrate the mechanism of operation.
Figure 7:
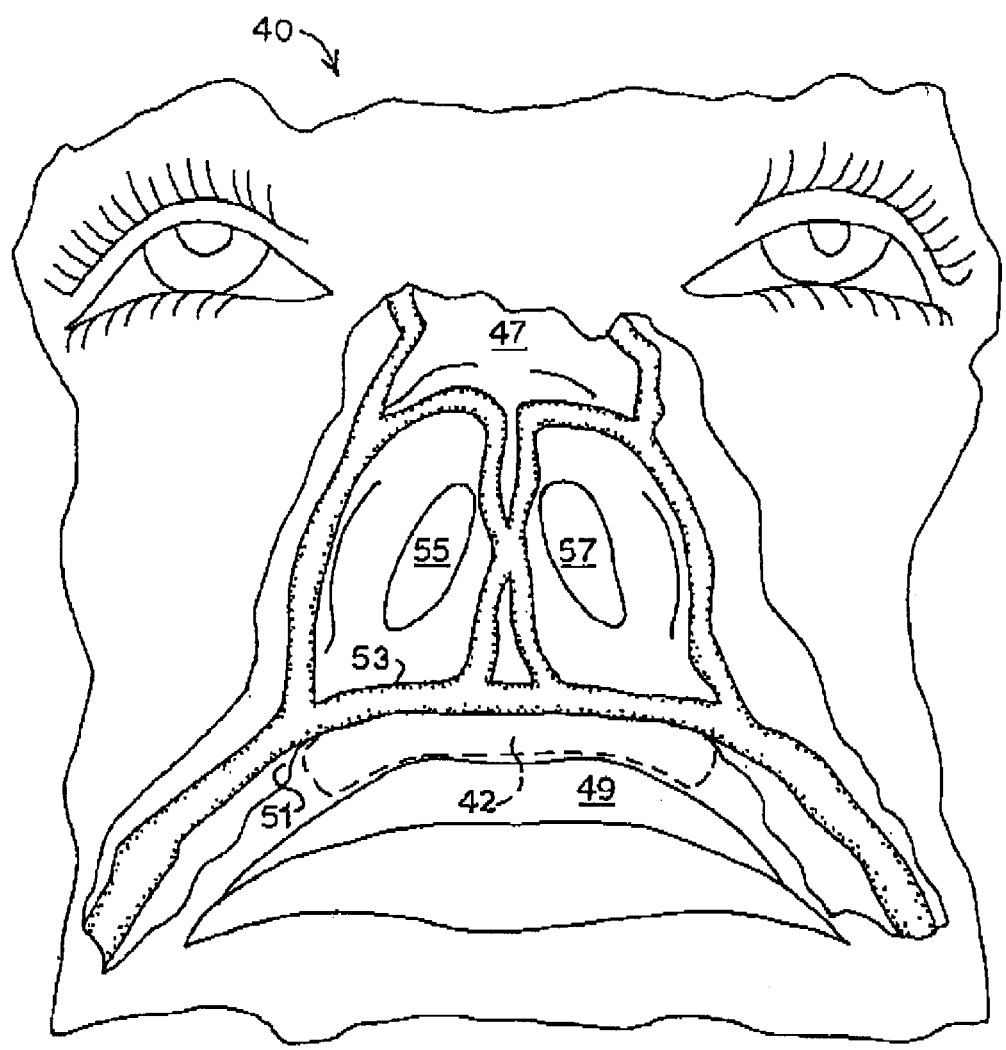
FIG. 7 shows a front view of the nasal area of a human face, with a portion of the outer layer of tissue cut-away in the nasal area to show schematically the anatomical configuration of the major arteries supplying blood to the nose in relation to the placement of an embodiment of the inventive nosebleed device to help illustrate the mechanism of operation.

FIG. 6 is a side elevation view and FIG. 7 is a frontal view upward from the chest, each with a portion of the outer layer of tissue cut-away to show the relation of arteries to the preferred location in a human face 40 for positioning an inventive nosebleed device/lip pack 42. To use the lip pack 42, an individual places the lip pack 42 intra-orally between the upper gum 43 and the portion 45 of the face 40 that is located below the nose 47 and above the top lip 49, preferably positioning the lip pack 42 as high as comfortably possible.

The natural tightness of the interface 51 between the upper gum 43 and the portion 45 olds the lip pack 42 in place. Through the natural tightness of the interface 51, the lip pack 42 suitably controls nasal bleeding by exerting pressure on the area of nasal vascularization 52, such as the superior labial artery 53, thus slowing blood flow to the Kiesselbach's plexus 54 and helping to enable natural coagulation mechanisms to occur so bleeding should stop. If desired, firmer pressure may be applied by pressing with a finger or fingers on the outside of the facial portion 45 just over the lip pack 42. When the nosebleed has stopped, the lip pack 42 is easily removed by the fingers or sliding the tongue.

An important advantage of this invention is that removal of the lip pack is typically pain-free and should not present a risk of re-bleeding because no devices are inserted into the nasal cavity. Another advantage of this invention is that when the lip pack 42 is positioned as described, the nasal cavities 55 and 57 remain unobstructed so the patient is able to breathe normally through the nose 47.

Figure 8:
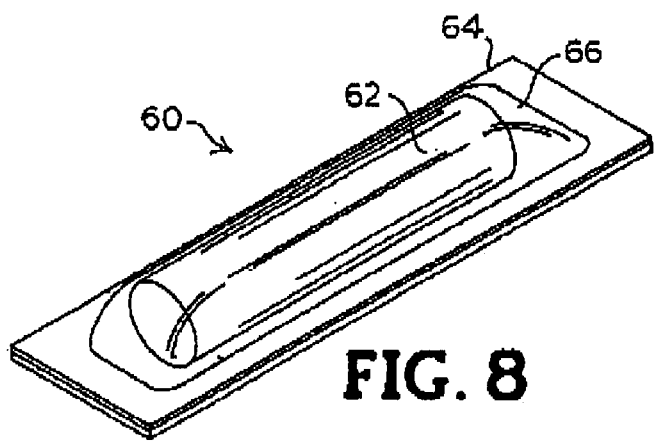
FIG. 8 shows a perspective view of a nosebleed package illustrating an embodiment of the inventive nosebleed device in combination with a container.

With respect to FIG. 8, illustrated is a perspective view of a nosebleed package 60 having, in combination, an inventive nosebleed device 62 disposed within a container 64. The nosebleed device 62 may be any of those described above or any obvious modifications of those described above, and should be sterile. The container 64 is sterile on the inside, and is illustrated here in one embodiment as a clear see-through blister packaging 66. Other packaging materials that are not see-through, such as paper or metal foil, may be used, and it is not intended to be limited to any particular kind of packaging materials. Packages 60 may be separate, or may be joined by perforations (not shown), the latter particularly being common with blister packaging. Such packaging lends itself well to a one-time use of the nosebleed device 62, after which it may be thrown away. Methods for packaging items for a medical use, where the item is sterilized and sealed inside a container with a sterile inside environment, typically using ethylene oxide for the sterilization, are well known to those of ordinary skill in the art.

Figure 9:
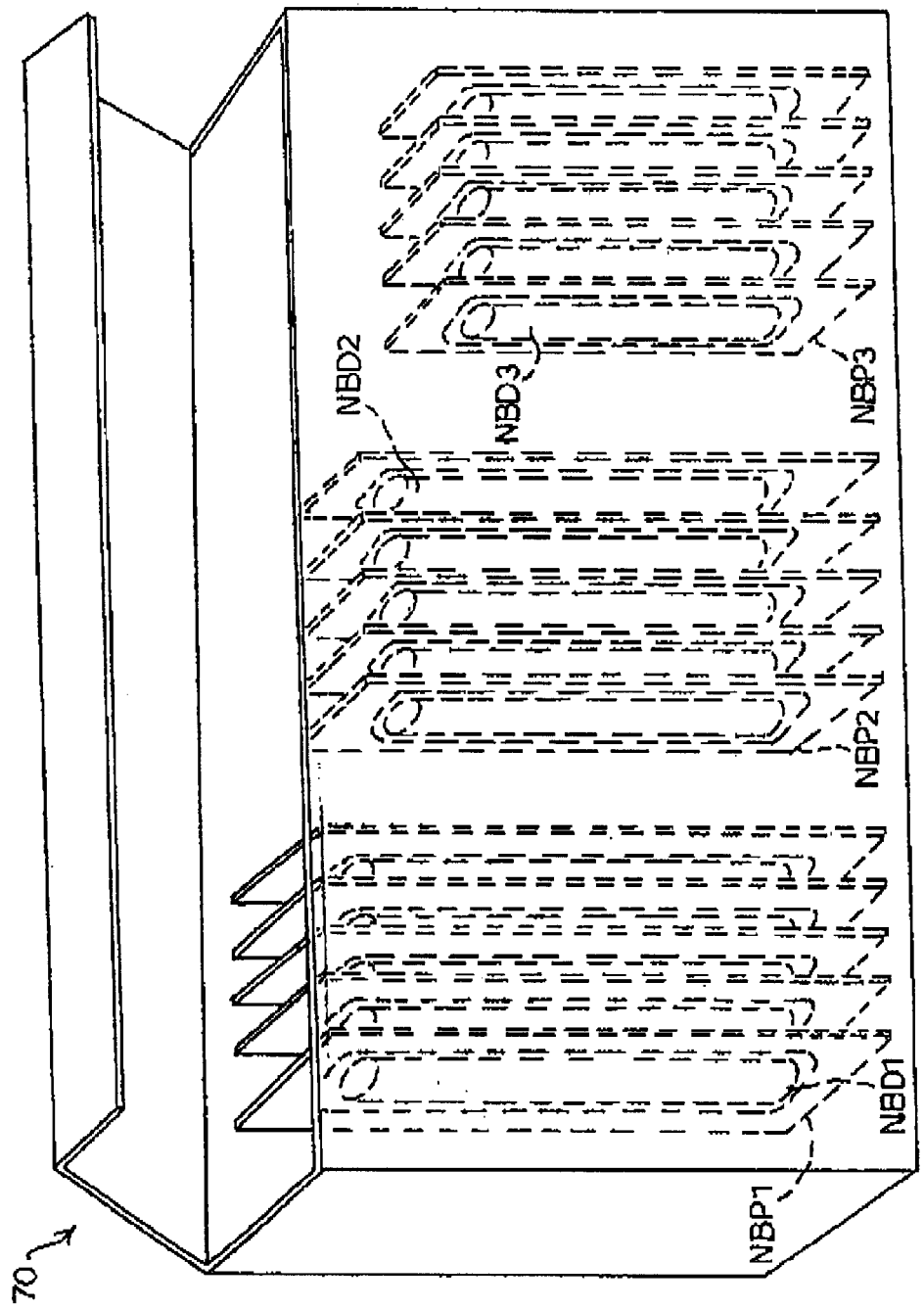
FIG. 9 shows a perspective view of a box containing a multiplicity of individual nosebleed packages that comprise individually packaged nosebleed devices each being disposed in a respective nosebleed container.

As depicted in FIG. 9, a box 70 may contain a multiplicity of individual nosebleed packages, which may be, as noted above, separate or joined by perforations. The nosebleed packages may all contain nosebleed devices of the same size or the nosebleed packages may contain nosebleed devices in various sizes, such as 2 different sizes, 3 different sizes, 4 different sizes, or more different sizes, in a manner similar to the way individually wrapped BAND-AIDS® are packed in a box for marketing.

For instance, box 70 may contain a multiplicity of individually packaged nosebleed devices comprising a first set of a plurality of nosebleed packages NBP1, such as 5 nosebleed packages NBP1 where each contains a large adult size nosebleed device NBD1, a second set of a plurality of nosebleed packages NBP2, such as 5 nosebleed packages NBP2 where each contains a next smaller adult size nosebleed package NBD2, and a third set of a plurality of nosebleed packages NBP3, such as 5 nosebleed packages NBP3 were each contains a child size nosebleed package 3, where the multiplicity of individual nosebleed packages NBP are conveniently packed together in the same box 70 for sale to consumers.

It will be appreciated that certain structural variations may suggest themselves to those skilled in the art. The present invention is not limited to the embodiments described above, but encompasses any and all embodiments within the scope of the following claims.

I claim:

1. A method of treating a nosebleed in a human having a nosebleed, the method comprising:

(a) providing a nosebleed device comprising an elongated body configured to be positioned between the upper gum and the portion of the face below the nose and above the top lip of the human;

(b) positioning the device between the upper gum and the portion of the face below the nose and above the top lip of the human so as to exert pressure on an area of nasal vascularization of the human; and (c) achieving alleviation of the nosebleed.

2. The method of claim 1, wherein the area of nasal vascularization is the superior labial artery, the anterior ethomoidal arteries, the posterior ethmoidal arteries, the sphenopalatine artery, or a combination thereof.

3. The method of claim 1, wherein the elongated body further includes compression padding longitudinally disposed on a portion of the elongated body.

4. The method of claim 1, wherein the elongated body is constructed of a material selected from the group consisting of gauze, cotton, polyurethane, rayon, rubber, polysorbate, polyvinyl alcohol, and combinations thereof.

5. The method of claim 1, wherein the elongated body is constructed of liquid-absorbent material.

6. The method of claim 1, wherein the elongated body has a diameter ranging from about 4 mm to about 12 mm.

7. The method of claim 1, wherein the elongated body has a length ranging from about 30 mm to about 80 mm.

8. The method of claim 1, wherein the elongated body has a first end and a second end, wherein at least one of the first end and second end is tapered.

9. A method of treating a nosebleed in a human having a nosebleed, the method comprising:
- (a) providing a nosebleed device comprising an elongated body from about 30 to about 80 mm in length and from about 4 to about 12 mm in diameter, wherein the body comprises a liquid-absorbent material having disposed thereon compression padding, wherein the padding has a thickness from about 1 to about 4 mm thick and a length from about a quarter to about two-thirds of the length of the device, so that the device is configured to be positioned between the upper gum and the portion of the face below the nose and above the top lip of the human;
- (b) positioning the device between the upper gum and the portion of the face below the nose and above the top lip of the human so as to exert pressure on an area of nasal vascularization of the human; and
- (c) achieving alleviation of the nosebleed.

* * * * *